(12) United States Patent
Zhuang et al.

(10) Patent No.: US 7,906,689 B2
(45) Date of Patent: Mar. 15, 2011

(54) CATALYST COMPOSITION AND PRODUCING PROCESS THEREOF FOR USE IN MANUFACTURING METHACROLEIN

(76) Inventors: Yan Zhuang, Shanghai (CN); Chunlei Zhang, Shanghai (CN); Xin Wen, Shanghai (CN); Jun Li, Shanghai (CN); Jingming Shao, Shanghai (CN); Peizhang Zhang, Shanghai (CN)

( * ) Notice: Subject to any disclaimer, the term of this patent is extended or adjusted under 35 U.S.C. 154(b) by 0 days.

(21) Appl. No.: 11/983,368

(22) Filed: Nov. 7, 2007

(65) Prior Publication Data

US 2009/0069605 A1    Mar. 12, 2009

(30) Foreign Application Priority Data

Sep. 12, 2007  (CN) .......................... 2007 1 0045865

(51) Int. Cl.
| | |
|---|---|
| C07C 45/00 | (2006.01) |
| B01J 23/00 | (2006.01) |
| B01J 21/00 | (2006.01) |
| B01J 29/00 | (2006.01) |
| B01J 37/00 | (2006.01) |

(52) U.S. Cl. ......... 568/479; 568/471; 502/248; 502/249; 502/255; 502/258; 502/308; 502/309; 502/311; 502/313; 502/314; 502/316; 502/317; 502/321; 502/322; 502/439

(58) Field of Classification Search .................. 502/248, 502/249, 255, 258, 308, 309, 311, 313, 314, 502/316, 317, 321, 322, 439; 568/471, 479
See application file for complete search history.

(56) References Cited

U.S. PATENT DOCUMENTS

| | | | | |
|---|---|---|---|---|
| 4,035,418 A | * | 7/1977 | Okada et al. | 562/538 |
| 4,217,309 A | * | 8/1980 | Umemura et al. | 568/477 |
| 4,250,339 A | * | 2/1981 | Sakamoto et al. | 568/471 |
| 4,259,211 A | * | 3/1981 | Krabetz et al. | 502/178 |
| 4,382,880 A | * | 5/1983 | Derrien | 502/313 |
| 4,388,223 A | * | 6/1983 | Ferlazzo et al. | 502/211 |
| 4,418,007 A | * | 11/1983 | Derrien | 502/312 |
| 4,438,217 A | * | 3/1984 | Takata et al. | 502/205 |
| 4,511,671 A | * | 4/1985 | Saito et al. | 502/242 |
| 4,537,874 A | * | 8/1985 | Sato et al. | 502/311 |
| 4,556,731 A | * | 12/1985 | Guttmann et al. | 562/546 |
| 4,732,884 A | * | 3/1988 | Sarumaru et al. | 502/205 |
| 4,837,191 A | * | 6/1989 | Glaeser et al. | 502/202 |
| 4,873,217 A | * | 10/1989 | Kawajiri et al. | 502/311 |
| 4,877,764 A | * | 10/1989 | Glaeser et al. | 502/209 |
| 5,166,119 A | * | 11/1992 | Oh-Kita et al. | 502/205 |
| 5,250,485 A | * | 10/1993 | Kuroda et al. | 502/159 |
| 5,491,258 A | * | 2/1996 | Watanabe et al. | 562/538 |
| 5,532,199 A | * | 7/1996 | Watanabe et al. | 502/311 |
| 5,583,086 A | * | 12/1996 | Tenten et al. | 502/249 |
| 5,637,546 A | * | 6/1997 | Tenten et al. | 502/312 |

(Continued)

*Primary Examiner* — Cam N Nguyen
(74) *Attorney, Agent, or Firm* — Raymond Y. Chan; David and Raymond Patent Firm

(57) ABSTRACT

A catalyst composition for use in manufacturing methacrolein by reacting with one of isobutene and t-butanol, the catalyst composition being represented by the formula of: x $(Mo_{12}Bi_aFe_bCo_cA_dB_eO_f)/y$ Z. $Mo_{12}Bi_aFe_bCo_cA_dB_eO_f$ is an oxide compound. Z is a catalyst carrier is one of graphite, boron, silicon, germanium powder, and a mixture thereof. Mo, Bi, Fe, Co, and O are chemical symbols of molybdenum, bismuth, iron, cobalt, and oxygen respectively. A is one of W, V, Ti, Zr, Nb, Ni, and Re. B is one of K, Rb, Cs, Sr, and Ba. The catalyst is adapted to not only enhance the production of methacrolein with high activeness and high selectivity but also effectively control the heat point of the catalyst during the methacrolein manufacturing process to prolong the catalyst life.

17 Claims, 4 Drawing Sheets

U.S. PATENT DOCUMENTS

| | | | | |
|---|---|---|---|---|
| 5,663,113 A * | 9/1997 | Midorikawa et al. | | 502/314 |
| 5,686,373 A * | 11/1997 | Tenten et al. | | 502/312 |
| 5,700,752 A * | 12/1997 | Kurimoto et al. | | 502/311 |
| 5,728,894 A * | 3/1998 | Nagano et al. | | 568/479 |
| 5,856,259 A * | 1/1999 | Watanabe et al. | | 502/305 |
| 5,885,922 A * | 3/1999 | Hibst et al. | | 502/305 |
| 5,910,608 A * | 6/1999 | Tenten et al. | | 562/532 |
| 5,981,804 A * | 11/1999 | Kurimoto et al. | | 568/479 |
| 6,383,973 B1 * | 5/2002 | Kimura et al. | | 502/300 |
| 6,383,976 B1 * | 5/2002 | Arnold et al. | | 502/311 |
| 6,429,332 B1 * | 8/2002 | Tanimoto et al. | | 562/532 |
| 6,784,134 B2 * | 8/2004 | Kasuga et al. | | 502/182 |
| 6,794,539 B2 * | 9/2004 | Unverricht et al. | | 562/535 |
| 6,797,839 B1 * | 9/2004 | Hibst et al. | | 562/532 |
| 6,878,847 B2 * | 4/2005 | Kasuga et al. | | 562/532 |
| 6,921,836 B1 * | 7/2005 | Hibst et al. | | 562/535 |
| 6,946,422 B2 * | 9/2005 | Stevenson et al. | | 502/311 |
| 7,012,039 B2 * | 3/2006 | Watanabe et al. | | 502/300 |

* cited by examiner

| | Chemical structure of catalyst composition |
|---|---|
| Example 1 | 80($Mo_{12}Bi_1Fe_{2.0}Co_{7.0}V_{0.2}Cs_{0.1}$)/20Si |
| Example 2 | 80($Mo_{12}Bi_1Fe_{2.0}Co_{7.0}V_{0.2}Cs_{0.1}$)/20B |
| Example 3 | 80($Mo_{12}Bi_1Fe_{2.0}Co_{7.0}V_{0.2}Cs_{0.1}$)/20Ge |
| Example 4 | 80($Mo_{12}Bi_1Fe_{2.0}Co_{7.0}V_{0.2}Cs_{0.1}$)/20C |
| Example 5 | 60($Mo_{12}Bi_1Fe_{2.0}Co_{7.0}V_{0.2}Cs_{0.1}$)/40Si |
| Example 6 | 80($Mo_{12}Bi_1Fe_{2.0}Co_{7.0}V_{0.2}Cs_{0.1}$)/20Si |
| Example 7 | 80($Mo_{12}Bi_1Fe_{2.0}Co_{7.0}V_{0.2}Cs_{0.1}$)/(10Si+10Ge) |
| Example 8 | 80($Mo_{12}Bi_1Fe_{2.0}Co_{7.0}V_{0.2}Cs_{0.1}$)/(10Si+10B) |
| Example 9 | 80($Mo_{12}Bi_1Fe_{2.0}Co_{7.0}Ti_{1.0}Cs_{0.1}$)/20Si |
| Example 10 | 80($Mo_{12}Bi_1Fe_{2.0}Co_{7.0}Zr_{1.0}Cs_{0.1}$)/20Si |
| Example 11 | 80($Mo_{12}Bi_1Fe_{2.0}Co_{7.0}Nb_{1.0}Cs_{0.1}$)/20Si |
| Example 12 | 80($Mo_{12}Bi_1Fe_{2.0}Co_{6.0}Ni_{1.0}Cs_{0.1}$)/20Si |
| Example 13 | 80($Mo_{12}Bi_1Fe_{2.0}Co_{7.0}V_{0.2}K_{0.1}$)/20Si |
| Example 14 | 80($Mo_{12}Bi_1Fe_{2.0}Co_{7.0}V_{0.2}Rb_{0.1}$)/20Si |
| Example 15 | 80($Mo_{12}Bi_1Fe_{2.0}Co_{7.0}V_{0.2}Ba_{0.1}$)/20Si |
| Comparison Example 1 | $Mo_{12}Bi_1Fe_{2.0}Co_{7.0}V_{0.2}Cs_{0.1}$ |
| Comparison Example 2 | 35($Mo_{12}Bi_1Fe_{2.0}Co_{7.0}V_{0.2}Cs_{0.1}$)/65Si |
| Comparison Example 3 | 95($Mo_{12}Bi_1Fe_{2.0}Co_{7.0}V_{0.2}Cs_{0.1}$)/5Si |
| Comparison Example 4 | $Mo_{12}Bi_1Fe_{2.0}Co_{7.0}Ti_{1.0}Cs_{0.1}$ |
| Comparison Example 5 | $Mo_{12}Bi_1Fe_{2.0}Co_{7.0}V_{0.2}K_{0.1}$ |

Table 1

| | Response Time (hr) | Salt Bath Temperature (°C) | Temp. Difference between salt bath and hotspot (°C) | Isobutene Conversion rate (%) | MAL Selectivity |
|---|---|---|---|---|---|
| Example 1 | 100 | 350 | 52 | 98.8 | 88.5 |
| | 4000 | 350 | 49 | 98.7 | 89.0 |
| Example 2 | 100 | 345 | 55 | 98.5 | 87.4 |
| | 4000 | 345 | 53 | 98.5 | 87.8 |
| Example 3 | 100 | 350 | 48 | 98.7 | 88.0 |
| | 4000 | 350 | 48 | 98.8 | 88.2 |
| Example 4 | 100 | 360 | 45 | 98.5 | 88.5 |
| | 4000 | 360 | 47 | 98.7 | 88.0 |
| Example 5 | 100 | 365 | 42 | 98.0 | 88.8 |
| | 4000 | 365 | 38 | 97.0 | 90.2 |
| Example 6 | 100 | 350 | 51 | 99.0 | 88.2 |
| | 4000 | 350 | 49 | 99.0 | 88.6 |
| Example 7 | 100 | 350 | 51 | 98.8 | 88.1 |
| Example 8 | 100 | 350 | 55 | 99.2 | 87.1 |
| Example 9 | 100 | 350 | 61 | 99.1 | 85.6 |
| Example 10 | 100 | 350 | 58 | 99.3 | 84.2 |
| Example 11 | 100 | 350 | 55 | 97.7 | 85.9 |
| Example 12 | 100 | 350 | 52 | 98.2 | 87.3 |
| Example 13 | 100 | 350 | 60 | 99.2 | 85.2 |
| Example 14 | 100 | 350 | 54 | 98.3 | 88.0 |
| Example 15 | 100 | 350 | 98 | 95.2 | 82.3 |
| Comparsion Example 1 | 100 | 330 | 78 | 95.6 | 80.2 |
| Comparsion Example 2 | 100 | 380 | 35 | 96.3 | 90.9 |
| Comparsion Example 3 | 100 | 330 | 75 | 95.7 | 82.5 |
| Comparsion Example 4 | 100 | 330 | 85 | 92.2 | 77.8 |
| Comparsion Example 5 | 100 | 330 | 82 | 92.6 | 78.5 |

Table 2

CATALYST COMPOSITION AND PRODUCING PROCESS THEREOF FOR USE IN MANUFACTURING METHACROLEIN

BACKGROUND OF THE PRESENT INVENTION

1. Field of Invention

The present invention relates to methacrolein, and more particularly to a catalyst composition and a producing process thereof for use in manufacturing methacrolein by using isobutene or t-butanol as the reacting agents to produce methacrolein with high activeness, high selectivity, and high stabilization properties.

2. Description of Related Arts

The oxidizing process of isobutene (or t-butanol) is widely used for manufacturing methacrolein in the industrialization production process of methyl methacrylate. Accordingly, there are two different processes for manufacturing methyl methacrylate by using C4 as the raw material. The first process includes a two-step oxidation process for isobutene (or t-butanol) to form methyl methacrylate, wherein the first step of oxidation of isobutene (or t-butanol) is to obtain methacrolein and the second step of oxidation of methacrolein is to obtain methylacrylic acid, such that the resulting methylacrylic acid reacts with methyl alcohol to form the methyl methacrylate through esterification. The second process includes a one-step oxidation process for isobutene (or t-butanol) to form methacrolein, which is then reacted with methanol (also commonly known as methyl alcohol) to form methyl methacrylate through oxidative esterification. Regardless the two different processes, isobutene (or t-butanol) in solid phase and the corresponding oxidation reaction for manufacturing catalyst of methacrolein are the main technical cores for the industrial production process.

There are lots of patents disclosing the process of isobutene (or t-butanol) to produce MAL and nearly all such patents teach the catalyst containing four major elements which are Mo, Bi, Fe, and Co in the composition. According to these patents, the common objective is that the four major elements incorporating with some trace elements are used to form the catalyst such that the trace elements are adjusted to achieve the relatively high activity and selectivity. However, there are two major drawbacks for such catalyst being applied in the industrial production process.

The first drawback is that when isobutene (or t-butanol) is oxidized to form methacrolein, a relatively huge amount of heat is generated, especially when catalyst is applied. The "overheat" not only causes the reaction in an uncontrolled manner but also drains the most main oxidized element Mo during reaction. In addition, the "overheat" will reduce the service life span of the catalyst. Although the Patents CN 1143946A (U.S. Pat. No. 5,728,894) and CN 1596149A (U.S. Pat. No. 7,012,039) teach the addition of Cerium (Ce) to provide thermal stability and reduction resistance to reduce the used up of Mo during reaction and to prolong the catalyst life, such Cerium cannot solve the "overheat" problem during reaction. At the same time, Cerium will reduce the selectivity of methacrolein in the process. Other Patents, such as CN1048540A and JP publication number 10614, suggest the using of inert material to dilute the oxide catalyst so as to enhance the heat conductivity of the oxide catalyst. However, it is inconvenient to dilute and load the oxide catalyst through the partition diluting method especially when the oxide catalyst is used in a relatively large reactor.

Another drawback is that when isobutene (or t-butanol) is oxidized to form methacrolein, the non-reacted isobutene will reduce the conversion rate not only to increase the consumption of raw material but also to reduce the efficiency of the process in an economical manner. In addition, it will poison the oxide catalyst during the second oxidation step of the first process for manufacturing methyl methacrylate, such that the life and activity of the oxide catalyst are greatly reduced. Therefore, in order to stabilize the reaction in a long term manner, the activity of catalyst should be relatively high in the methacrolein manufacturing process or the reaction should be maintained under a higher temperature. However, such two above mentioned methods will reduce the selectivity of methacrolein. All patents, including U.S. Pat. No. 4,217,309, U.S. Pat. No. 4,250,339, U.S. Pat. No. 4,258,217, U.S. Pat. No. 4,267,385, U.S. Pat. No. 4,306,088, U.S. Pat. No. 4,354,044, U.S. Pat. No. 4,446,328, U.S. Pat. No. 4,511,671, U.S. Pat. No. 5,144,090, U.S. Pat. No. 5,245,083, U.S. Pat. No. 5,583,086, U.S. Pat. No. 5,728,894, did not teach how to maintain the high selectivity of methacrolein while the isobutene is under high conversion rate.

SUMMARY OF THE PRESENT INVENTION

A main object of the present invention is to provide a catalyst composition and a producing process thereof for use in manufacturing methacrolein by reacting with isobutene or t-butanol to produce methacrolein with high activity, high selectivity, and high stability.

Another object of the present invention is to provide a catalyst composition and a producing process thereof, which comprises an oxide compound of Mo, Bi, Fe, and Co in powder form and an enhancement element of at least one of W, V, Ti, Zr, Nb, Ni, and Re mixing with the oxide compound to enhance the oxidation process of isobutene or t-butanol to produce methacrolein.

Another object of the present invention is to provide a catalyst composition and a producing process thereof, wherein the catalyst composition can effectively lower the temperature at the heat point (hotspot) of the catalyst during the methacrolein manufacturing process so as to prolong the catalyst life.

Another object of the present invention is to provide a catalyst composition and a producing process thereof, wherein the catalyst composition enhances the activity thereof by increasing the reaction temperature (salt bath temperature) without affecting the selectivity of methacrolein, so as to reduce the further oxidization of methacrolein by isobutene.

Accordingly, in order to accomplish the objective, the present invention provides a catalyst composition for use in manufacturing methacrolein by reacting with one member selected from the group consisting of isobutene and t-butanol, the catalyst composition being represented by the formula of:

$$x(Mo_{12}Bi_aFe_bCo_cA_dB_eO_f)/yZ$$

wherein $Mo_{12}Bi_aFe_bCo_cA_dB_eO_f$ is an oxide compound. Z is a catalyst carrier having a granularity smaller than 40 meshes and is selected from the group consisting of graphite, boron, silicon, germanium powder, and a mixture thereof. Mo, Bi, Fe, Co, and O are chemical symbols of molybdenum, bismuth, iron, cobalt, and oxygen respectively. A is at least one member selected from the group consisting of W, V, Ti, Zr, Nb, Ni, and Re. B is at least one member selected from the group consisting of K, Rb, Cs, Sr, and Ba. a, b, c, d, and e are the atomic ratios of Mo, Bi, Fe, Co, A, and B respectively, wherein a=0.1 to 15, b=0.05 to 10, c=1 to 15, d=0.01 to 5, e=0.01 to 2. f is determined by the atomic ratios of each component of the oxide compound. x and y represent the active constituent of the oxide compound and the quantity of the carrier Z by percentage weight respectively. y/(x+y)=0.1 to 70% by weight, preferably 10 to 50% by weight.

Accordingly, the process of producing the catalyst composition comprises the steps of:

(a) individually dissolving each component of the oxide compound in proportional ratio.

(b) mixing the components with each other to form a mixture and adding ammonia water into the mixture to adjust a pH value thereof between 4 and 7.

(c) adding the carrier Z into the mixture in powdered form to form a compound powder; and (d) drying the compound powder to form the catalyst composition.

Using the above mentioned catalyst composition with isobutene (or t-butanol) in gas phase, the process of manufacturing synthesis MAL comprises the steps of:

(a) preheating the raw material of isobutene (or t-butanol) with oxygen containing gas and steam to form a reactant, wherein the oxygen containing gas can be the air or diluted gas with oxygen molecules; and (b) introducing the reactant into a guiding tube of a catalyst bed of a reactor which is loaded with the catalyst composition to oxidize the reactant to form the synthesis MAL.

These and other objectives, features, and advantages of the present invention will become apparent from the following detailed description, the accompanying drawings, and the appended claims.

Table 1 illustrates different chemical compositions of the catalyst composition according to the above preferred embodiment of the present invention.

Table 2 illustrates the oxidation reaction conditions and results of examples 1 to 15 and comparison examples 1 to 5 of the catalyst composition according to the above preferred embodiment of the present invention.

DETAILED DESCRIPTION OF THE PREFERRED EMBODIMENT

According to the present invention, a catalyst composition for use in manufacturing methacrolein is illustrated, wherein the catalyst composition is used in the manufacturing process by reacting with one member selected from the group consisting of isobutene and t-butanol.

The catalyst composition is represented by the formula of:

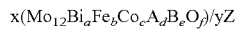

$$x(Mo_{12}Bi_aFe_bCo_cA_dB_eO_f)/yZ$$

Accordingly, $Mo_{12}Bi_aFe_bCo_cA_dB_eO_f$ is an oxide compound. Z is a catalyst carrier having a granularity smaller than 40 meshes and is selected from the group consisting of graphite, boron, silicon, germanium powder, and a mixture thereof. Mo, Bi, Fe, Co, and O are chemical symbols of molybdenum, bismuth, iron, cobalt, and oxygen respectively. A is at least one member selected from the group consisting of W, V, Ti, Zr, Nb, Ni, and Re. B is at least one member selected from the group consisting of K, Rb, Cs, Sr, and Ba. a, b, c, d, and e are the atomic ratios of Mo, Bi, Fe, Co, A, and B respectively, wherein a=0.1 to 15, b=0.05 to 10, c=1 to 15, d=0.01 to 5, e=0.01 to 2. f is determined by the atomic ratios of each component of the oxide compound. x and y represent the active constituent of the oxide compound and the quantity of the carrier Z by percentage weight respectively. Accordingly, x and y satisfy the requirements of the formula: y/(x+y)=0.1 to 70% by weight, preferably 10 to 50% by weight.

The catalyst composition is prepared by compositions comprising molybdic compound selected from the group consisting of phospho-molybdic acid, molybdate, and molybdenum oxide; vanadium compound selected from the group consisting of metavanadate or vanadium pentoxide; tungsten compound selected from the group consisting of tungstate and tungsten trioxide; alkaline element, such as alkaline metal or alkali earth metal compound, selected from the group consisting of hydroxide and nitrate; and other essential elements selected from the group consisting of nitrate, acetate, chloride, and oxide compound.

Figure 1:
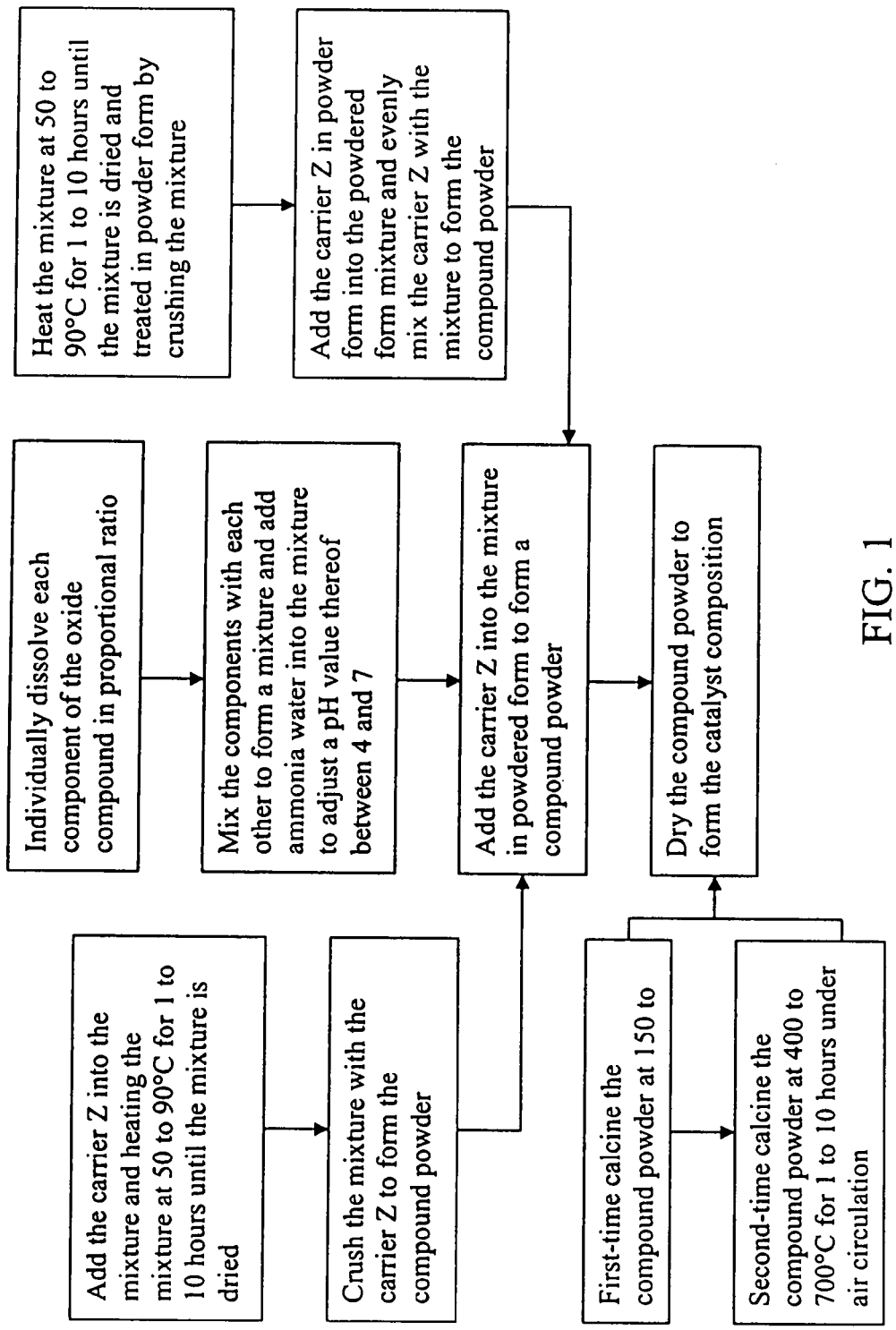
FIG. 1 is a flow diagram illustrating a process of producing the catalyst composition for manufacturing methacrolein and its alternative according to a preferred embodiment of the present invention.

As shown in FIG. 1, the present invention further provides a process of producing the catalyst composition comprising the following steps.

(1) Individually dissolve each component of the oxide compound in proportional ratio.

(2) Mix the components with each other to form a mixture and adjust a pH value of the mixture to a range between 4 and 7 by adding ammonia water.

(3) Add the carrier Z into the mixture to form a compound powder.

(4) Dry the compound powder to form the catalyst composition.

Accordingly, the step (3) of the present invention further comprises the following steps.

(3.1) Add the carrier Z into the mixture and ripen the mixture at 50 to 90° C. for 1 to 10 hours until the mixture is dried.

(3.2) Crush the mixture with the carrier Z to form the compound powder.

In addition, the step (4) of the present invention further comprises the following steps.

(4.1) First-time calcine the compound powder at 150 to 250° C.

(4.2) Second-time calcine the compound powder at 400 to 700° C. for 1 to 10 hours under air circulation.

Alternatively, the step (3) of the present invention further comprises the following steps.

(3.1') Heat the mixture at 50 to 90° C. by ripening for 1 to 10 hours until the mixture is dried and treated in powder form by crushing the mixture.

(3.2') Add the carrier Z in powder form into the powdered form mixture and evenly mix the carrier Z with the mixture to form the compound powder by a mixing machine.

Figure 2:
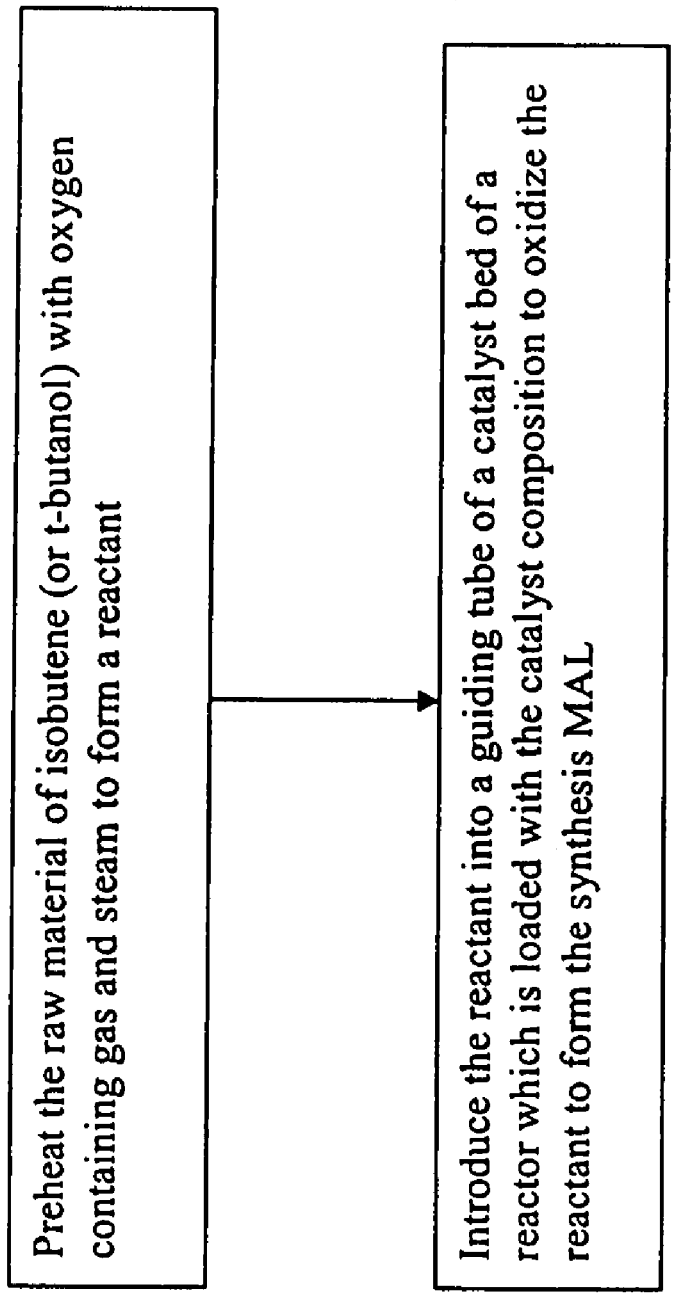
FIG. 2 is a flow diagram illustrating a process of producing methacrolein with the catalyst composition according to the above preferred embodiment of the present invention.

As shown in FIG. 2, using the above mentioned catalyst composition with isobutene (or t-butanol) in gaseous phase, the process of manufacturing synthesis MAL comprises the steps of:

(A) Preheat the raw material of isobutene (or t-butanol) with oxygen containing gas and steam to form a reactant, wherein the oxygen containing gas can be air or diluted gas with oxygen molecules.

(B) Introduce the reactant into a guiding tube of a catalyst bed of a reactor which is loaded with the catalyst composition to oxidize the reactant to form the synthesis MAL.

Accordingly, the oxygen containing gas can be a mixture of diluted gas with oxygen molecules. The oxygen molecule of the oxygen containing gas can be derived from pure oxygen gas, rich oxygen gas, or air. Diluted gas can be at least one of $N_2$, CO, $CO_2$, or $H_2O$.

The conditions for oxidizing reaction of isobutene (or t-butanol) is: Temperature at 300 to 500° C., optimized temperature at 370 to 450° C.; Pressure at 0.05 to 0.5 MPa, optimized pressure at atmosphere pressure; Space velocity of the gaseous mixture between 500 and 5000 $h^{-1}$, optimized space velocity between 800 and 3200 $h^{-1}$. The mole concentration of isobutene (or t-butanol) is 1 to 20%, optimized mole concentration is 3 to 10%. The mole ratio of isobutene (or t-butanol):$O_2$ is 1:1~10, optimized mole ratio is 1:2~6. The mole ratio of isobutene (or t-butanol):steam is 1:1~15, optimized mole ratio is 1:1.5~8. During the reaction, the relationship between the conversion rate of the raw material and the selectivity of MAL is determined by the following formulas.

Conversion rate of isobutene (or $t$-butanol) =

$$\frac{\text{Number of moles of isobutene(or } t\text{-butanol) being used up}}{\text{Number of moles of isobutene (or } t\text{-butanol) being introduced}} \times 100\%$$

Selectivity of $MAL$ =

$$\frac{\text{Number of moles of } MAL \text{ being formed}}{\text{Number of moles of isobutene (or } t\text{-butanol) being used up}} \times 100\%$$

Example 1

The catalyst composition has a chemical structure of $80(Mo_{12}Bi_1Fe_{2.0}Co_{7.0}V_{0.2}Cs_{0.1})/20Si$, as shown in Table 1, wherein the process of producing the catalyst composition comprises the following steps.

(1) Dissolve 3,000 grams of Ammonium heptamolybdate $((NH_4)_6Mo_7O_{24}\cdot 4H_2O)$ and 33.1 grams of Ammonium metavanadate $(NH_4VO_3)$ into 5 liters of distilled water at 40° C. to obtain solution A.

(2) Dissolve 687 grams of Bismuth(III) nitrate pentahydrate $(Bi(NO_3)_3\cdot 5H_2O)$, 1,156 grams of Iron(III) nitrate nonahydrate $(FeNO_3\cdot 9H_2O)$, 2,885 grams of Cobalt nitrate hexahydrate $(Co(NO_3)_2\cdot 6H_2O)$, and 27.5 grams of cesium nitrates into 1 liter of 15% weight diluted nitric acid $(HNO_3)$ to obtain solution B.

(3) Add the solution A into the solution B while stirring the solution B, then add ammonia water to adjust the pH value to 6 so as to obtain a pulpous solution with relatively high viscosity.

(4) Stir and heat the pulpous solution at 70° C. for ripening for 4 hours.

(5) Evaporate the pulpous solution at 100° C. until the pulpous solution changes from fluid state (liquid state) to solid state, and then calcine the pulpous solution in solid state at 200° C. for 5 hours under ambient conditions to obtain 4 kilograms of sample powder.

(6) Evenly mix 1,000 grams of elemental silicon powder (having a size smaller than 40 meshes) with the sample powder via a mixing machine to form a mixture powder.

(7) Add 500 milliliters of distilled water to the mixture powder and mold the mixture powder to form a catalyst granule in granular form having an outer diameter of 5 mm, an inner diameter of 1.5 mm and a length of 5 mm.

(8) Calcine the catalyst granule at 550° C. for 5 hours to form the catalyst composition in granular form as a final product.

The process of producing MAL with the catalyst composition comprises the following steps.

(1) Load the catalyst composition in one at least 3 meter long guiding tube of a catalyst bed of a reactor.

(2) Introduce isobutene, water, oxygen, nitrogen with a mole ratio of 1:1.5:2:12 into the reactor for selective oxidation process under the following conditions: space velocity at 1200 $h^{-1}$ (standard condition); atmospheric pressure and salt bath temperature at 350° C. Accordingly, the hot spot temperature is 402° C. and the difference between the salt bath temperature and the hot spot temperature is 52° C.

Accordingly, the result for 100-hour response time (reaction time) is that the conversion rate of isobutene is 98.8% and the selectivity of MAL is 88.5%. The result after 4,000-hour response time is that the hot spot temperature is 399° C., the isobutene conversion rate is 98.7% and the selectivity of MAL is 89.0%. As a result, the activeness (or activity) of the catalyst is almost remained constant while the selectivity of MAL is slightly increased. The catalyst composition is shown in Table 1 and the corresponding detail result of the Example 1 is shown in Table 2.

Example 2

According to the Table 2, the steps in the process of producing the catalyst composition in Example 2 are the same steps as shown in Example 1, except that the 1,000 grams of elemental silicon powder in the step (6) is substituted by 1,000 grams of boron powder having a size smaller than 40 meshes. Accordingly, under the same condition and process as in Example 1, the catalyst composition having the chemical structure of $80(Mo_{12}Bi_1Fe_{2.0}Co_{7.0}V_{0.2}Cs_{0.1})/20B$ is formed by boron powder. The detail result of the Example 2 is shown in Table 2.

Example 3

According to the Table 2, the steps in the process of producing the catalyst composition in Example 3 are the same steps as shown in Example 1, except that the 1,000 grams of elemental silicon powder in the step (6) is substituted by 1,000 grams of germanium powder having a size smaller than 40 meshes. Accordingly, under the same condition and process as in Example 1, the catalyst composition having the chemical structure of $80(Mo_{12}Bi_1Fe_{2.0}Co_{7.0}V_{0.2}Cs_{0.1})/20Ge$ is formed by germanium powder. The detail result of the Example 3 is shown in Table 2.

Example 4

According to the Table 2, the steps in the process of producing the catalyst composition in Example 4 are the same steps as shown in Example 1, except that the 1,000 grams of elemental silicon powder in the step (6) is substituted by 1,000 grams of graphite powder having a size smaller than 40 meshes. Accordingly, under the same condition and process as in Example 1, the catalyst composition having the chemical structure of $80(Mo_{12}Bi_1Fe_{2.0}Co_{7.0}V_{0.2}Cs_{0.1})/20C$ is formed by graphite powder. The detail result of the Example 4 is shown in Table 2.

Comparison Example 1

According to the Table 2, the steps in the process of producing the catalyst composition in Comparison Example 1 are the same steps as shown in Example 1, except that the 1,000 grams of elemental silicon powder in the step (6) is omitted. Accordingly, under the same condition and process as in Example 1, the catalyst composition having the chemical structure of $Mo_{12}Bi_1Fe_{2.0}Co_{7.0}V_{0.2}Cs_{0.1}$ is formed without elemental silicon powder. The detail result of the Comparison Example 1 is shown in Table 2.

Example 5

According to the Table 2, the steps in the process of producing the catalyst composition in Example 5 are the same steps as shown in Example 1, except that the 1,000 grams of elemental silicon powder in the step (6) is substituted by 2,670 grams of elemental silicon powder having a size smaller than 40 meshes. Accordingly, under the same condition and process as in Example 1, the catalyst composition having the chemical structure of $60(Mo_{12}Bi_1Fe_{2.0}Co_{7.0}V_{0.2}Cs_{0.1})/40Si$ is formed by increasing the amount of elemental silicon powder. The detail result of the Example 5 is shown in Table 2.

Example 6

The catalyst composition has a chemical structure of $80(Mo_{12}Bi_1Fe_{2.0}Co_{7.0}V_{0.2}Cs_{0.1})/20Si$, as shown in Table 1, wherein the process of producing the catalyst composition comprises the following steps.

(1) Dissolve 3,000 grams of Ammonium heptamolybdate $((NH_4)_6Mo_7O_{24}.4H_2O)$ and 33.1 grams of Ammonium metavanadate $(NH_4VO_3)$ into 5 liters of distilled water at 40° C. to obtain solution A.

(2) Dissolve 687 grams of Bismuth(III) nitrate pentahydrate $(Bi(NO_3)_3.5H_2O)$, 1,156 grams of Iron(III) nitrate nonahydrate $(FeNO_3.9H_2O)$, 2,885 grams of Cobalt nitrate hexahydrate $(Co(NO_3)_2.6H_2O)$, and 27.5 grams of cesium nitrates into 1 liter of 15% (by weight) diluted nitric acid $(HNO_3)$ to obtain solution B.

(3) Stir the solution B and add the solution A to the solution B while stirring, then add ammonia water to adjust the pH value to 6 so as to obtain a pulpous solution with relatively high viscosity.

(4) Mix 1,000 grams of elemental silicon powder (having a size smaller than 40 meshes) with the pulpous solution to form a pulpous mixture.

(5) Stir and heat the pulpous mixture at 70° C. for ripening for 4 hours.

(6) Evaporate the pulpous mixture at 100° C. until the pulpous mixture changes from fluid state (liquid state) to solid state, and then calcine the pulpous mixture in solid state at 200° C. for 5 hours in the air atmosphere (under ambient conditions) to obtain 5 kilograms of mixture powder.

(7) Add 500 milliliters of distilled water to the mixture powder and mold the mixture powder to form a catalyst granule in granular form having an outer diameter of 5 mm, an inner diameter of 1.5 mm and a length of 5 mm.

(8) Calcine the catalyst granule at 550° C. for 5 hours to form the catalyst composition in granular form as a final product.

Accordingly, under the same condition and MAL manufacturing process as in Example 1, MAL is formed by using the above mentioned catalyst composition. The detail result of the Example 6 is shown in Table 2.

Example 7

According to the Table 2, the steps in the process of producing the catalyst composition in Example 7 are the same steps as shown in Example 1, except that the 1,000 grams of elemental silicon powder in the step (6) is substituted by 500 grams of elemental silicon powder having a size smaller than 40 meshes and 500 grams of germanium powder having a size smaller than 40 meshes. Accordingly, under the same condition and process as in Example 1, the catalyst composition having the chemical structure of $80(Mo_{12}Bi_1Fe_{2.0}Co_{7.0}V_{0.2}Cs_{0.1})/(10Si+10Ge)$ is formed by a combination of elemental silicon powder and germanium powder. The detail result of the Example 7 is shown in Table 2.

Example 8

According to the Table 2, the steps in the process of producing the catalyst composition in Example 8 are the same steps as shown in Example 1, except that the 1,000 grams of elemental silicon powder in the step (6) is substituted by 500 grams of elemental silicon powder having a size smaller than 40 meshes and 500 grams of boron powder having a size smaller than 40 meshes. Accordingly, under the same condition and process as in Example 1, the catalyst composition having the chemical structure of $80(Mo_{12}Bi_1Fe_{2.0}Co_{7.0}V_{0.2}Cs_{0.1})/(10Si+10B)$ is formed by a combination of elemental silicon powder and boron powder. The detail result of the Example 8 is shown in Table 2.

Example 9

According to the Table 2, the steps in the process of producing the catalyst composition in Example 9 are the same steps as shown in Example 1, except that the 33.1 grams of Ammonium metavanadate $(NH_4VO_3)$ in the step (1) is substituted by 114.5 grams of titanium dioxide. Accordingly, under the same condition and process as in Example 1, the catalyst composition having the chemical structure of $80(Mo_{12}Bi_1Fe_{2.0}Co_{7.0}Ti_{1.0}Cs_{0.1})/20Si$ is formed by titanium dioxide. The detail result of the Example 9 is shown in Table 2.

Example 10

According to the Table 2, the steps in the process of producing the catalyst composition in Example 10 are the same steps as shown in Example 9, except that the 114.5 grams of titanium dioxide in the step (1) is substituted by 176.3 grams of zirconium dioxide. Accordingly, under the same condition and process as in Example 1, the catalyst composition having the chemical structure of $80(Mo_{12}Bi_1Fe_{2.0}Co_{7.0}Zr_{1.0}Cs_{0.1})/20Si$ is formed by titanium dioxide. The detail result of the Example 10 is shown in Table 2.

Example 11

According to the Table 2, the steps in the process of producing the catalyst composition in Example 11 are the same steps as shown in Example 9, except that the 114.5 grams of titanium dioxide in the step (1) is substituted by 380.2 grams of di-niobium pentoxide. Accordingly, under the same condition and process as in Example 1, the catalyst composition having the chemical structure of $80(Mo_{12}Bi_1Fe_{2.0}Co_{7.0}Nb_{1.0}Cs_{0.1})/20Si$ is formed by di-niobium pentoxide. The detail result of the Example 11 is shown in Table 2.

Example 12

According to the Table 2, the steps in the process of producing the catalyst composition in Example 12 are the same steps as shown in Example 1, except that the 2,885 grams of Cobalt nitrate hexahydrate $(Co(NO_3)_2.6H_2O)$ in the step (2)

is substituted by 2,473 grams of Cobalt nitrate hexahydrate $(Co(NO_3)_2.6H_2O)$ and 416 grams of Nickel nitrate hexahydrate. Accordingly, under the same condition and process as in Example 1, the catalyst composition having the chemical structure of $80(Mo_{12}Bi_1Fe_{2.0}Co_{6.0}Ni_{1.0}Cs_{0.1})/20Si$ is formed by a combination of Cobalt nitrate hexahydrate and Nickel nitrate hexahydrate. The detail result of the Example 12 is shown in Table 2.

Example 13

According to the Table 2, the steps in the process of producing the catalyst composition in Example 13 are the same steps as shown in Example 1, except that the 27.5 grams of cesium nitrates in the step (2) is substituted by 14.25 grams of anhydrous potassium nitrate. Accordingly, under the same condition and process as in Example 1, the catalyst composition having the chemical structure of $80(Mo_{12}Bi_1Fe_{2.0}Co_{7.0}V_{0.2}K_{0.1})/20Si$ is formed by anhydrous potassium nitrate. The detail result of the Example 13 is shown in Table 2.

Example 14

According to the Table 2, the steps in the process of producing the catalyst composition in Example 14 are the same steps as shown in Example 1, except that the 27.5 grams of cesium nitrates in the step (2) is substituted by 20.78 grams of anhydrous rubidium nitrate. Accordingly, under the same condition and process as in Example 1, the catalyst composition having the chemical structure of $80(Mo_{12}Bi_1Fe_{2.0}Co_{7.0}V_{0.2}Rb_{0.1})/20Si$ is formed by anhydrous rubidium nitrate. The detail result of the Example 14 is shown in Table 2.

Example 15

According to the Table 2, the steps in the process of producing the catalyst composition in Example 15 are the same steps as shown in Example 1, except that the 27.5 grams of cesium nitrates in the step (2) is substituted by 36.82 grams of anhydrous barium nitrate. Accordingly, under the same condition and process as in Example 1, the catalyst composition having the chemical structure of $80(Mo_{12}Bi_1Fe_{2.0}Co_{7.0}V_{0.2}Ba_{0.1})/20Si$ is formed by anhydrous barium nitrate. The detail result of the Example 15 is shown in Table 2.

Comparison Example 2

According to the Table 2, the steps in the process of producing the catalyst composition in Comparison Example 2 are the same steps as shown in Example 1, except that the 1,000 grams of elemental silicon powder in the step (6) is substituted by 7.5 kilograms of elemental silicon powder. Accordingly, under the same condition and process as in Example 1, the catalyst composition having the chemical structure of $35(Mo_{12}Bi_1Fe_{2.0}Co_{7.0}V_{0.2}Cs_{0.1})65Si$ is formed by increasing the amount of elemental silicon powder. The detail result of the Comparison Example 2 is shown in Table 2.

Comparison Example 3

According to the Table 2, the steps in the process of producing the catalyst composition in Comparison Example 3 are the same steps as shown in Example 1, except that the 1,000 grams of elemental silicon powder in the step (6) is substituted by 210 grams of elemental silicon powder. Accordingly, under the same condition and process as in Example 1, the catalyst composition having the chemical structure of $95(Mo_{12}Bi_1Fe_{2.0}Co_{7.0}V_{0.2}Cs_{0.1})5Si$ is formed by decreasing the amount of elemental silicon powder. The detail result of the Comparison Example 3 is shown in Table 2.

Comparison Example 4

According to the Table 2, the steps in the process of producing the catalyst composition in Comparison Example 4 are the same steps as shown in Example 9, except that the elemental silicon powder in the step (6) is omitted. Accordingly, under the same condition and process as in Example 1, the catalyst composition having the chemical structure of $Mo_{12}Bi_1Fe_{2.0}Co_{0.7}Ti_{1.0}Cs_{0.1}$ is formed without the elemental silicon powder. The detail result of the Comparison Example 4 is shown in Table 2.

Comparison Example 5

According to the Table 2, the steps in the process of producing the catalyst composition in Comparison Example 5 are the same steps as shown in Example 13, except that the elemental silicon powder in the step (6) is omitted. Accordingly, under the same condition and process as in Example 1, the catalyst composition having the chemical structure of $Mo_{12}Bi_1Fe_{2.0}Co_{7.0}Ti_{1.0}Cs_{0.1}$ is formed without elemental silicon powder. The detail result of the Comparison Example 5 is shown in Table 2.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A process of manufacturing synthesis MAL comprises the steps of:
   (a) preheating one member selected from the group consisting of isobutene and t-butanol with oxygen containing gas and steam to form a reactant; and
   (b) introducing said reactant into a reactor which is loaded with a catalyst composition to incorporate with said reactant to form a synthesis MAL, said catalyst composition being represented by the formula of: $x(Mo_{12}Bi_aFe_bCo_cA_dB_eO_f)/yZ$ wherein $Mo_{12}Bi_aFe_bCo_cA_dB_eO_f$ is an oxide compound, wherein Z is a catalyst carrier selected from the group consisting of graphite, boron, silicon, germanium powder, and mixtures thereof, wherein Mo, Bi, Fe, Co, and O are chemical symbols of molybdenum, bismuth, iron, cobalt, and oxygen respectively, wherein A is at least one member selected from the group consisting of W, V, Ti, Zr, Nb, Ni, and Re, wherein B is at least one member selected from the group consisting of K, Rb, Cs, Sr, and Ba, wherein a, b, c, d, and e are the atomic ratios of Mo, Bi, Fe, Co, A, and B respectively, wherein f is determined by the atomic ratios of each component of said oxide compound, wherein x and y represent the quantity of said oxide compound and the quantity of said carrier Z respectively, wherein a, b, c, d, e and f satisfy the requirement of a=0.1 to 15, b=0.05 to 10, c=1 to 15, d=0.01 to 5, e=0.01 to 2; wherein said x and said y has a relationship determined by a formula of y/(x+y).

2. The process, as recited in claim 1, wherein a, b, c, d, and f satisfy the requirements of a=0.1 to 15, b=0.05 to 10, c=1 to 15, d=0.01 to 5, e=0.01 to 2, wherein x and y satisfy the requirements of the formula: y/(x+y)=0.1 to 70% by weight, wherein said catalyst composition is prepared by compositions comprising molybdic compound selected from the group consisting of phospho-molybdic acid, molybdate, and molybdenum oxide, vanadium compound selected from the group consisting of metavanadate or vanadium pentoxide, tungsten compound selected from the group consisting of tungstate and tungsten trioxide, alkaline element selected from the group consisting of hydroxide and nitrate, and other essential elements selected from the group consisting of nitrate, acetate, chloride, and oxide compound.

3. The process, as recited in claim 2, wherein said oxygen containing gas is a mixture of diluted gas with oxygen molecules, wherein said oxygen molecules of said oxygen containing gas is selected from the group consisting of pure oxygen gas, rich oxygen gas, and the air, wherein said diluted gas is selected from the group consisting of $N_2$, CO, $CO_2$, and $H_2O$.

4. The process, as recited in claim 3, wherein a condition for said reactant in said reactor is: temperature at 300 to 500° C.; Pressure at 0.05 to 0.5 MPa; space velocity of gaseous mixture is 500 to 5000 $hs^{-1}$; the mole concentration of member is 1 to 20%; the mole ratio between said member and $O_2$ is 1:1-10; and the mole ratio between said member and steam is 1:1-15.

5. The process, as recited in claim 2, wherein a condition for said reactant in said reactor is: temperature at 300 to 500° C.; Pressure at 0.05 to 0.5 MPa; space velocity of gaseous mixture is 500 to 5000 $hs^{-1}$; the mole concentration of member is 1 to 20%; the mole ratio between said member and $O_2$ is 1:1-10; and the mole ratio between said member and steam is 1:1-15.

6. The process, as recited in claim 1, wherein said oxygen containing gas is a mixture of diluted gas with oxygen molecules, wherein said oxygen molecules of said oxygen containing gas is selected from the group consisting of pure oxygen gas, rich oxygen gas, and the air, wherein said diluted gas is selected from the group consisting of $N_2$, CO, $CO_2$, and $H_2O$.

7. The process, as recited in claim 1, wherein a condition for said reactant in said reactor is: temperature at 300 to 500° C.; Pressure at 0.05 to 0.5 MPa; space velocity of gaseous mixture is 500 to 5000 $hs^{-1}$; the mole concentration of member is 1 to 20%; the mole ratio between said member and $O_2$ is 1:1-10; and the mole ratio between said member and steam is 1:1-15.

8. A catalyst composition for use in manufacturing methacrolein by reacting with one member selected from the group consisting of isobutene and t-butanol, the catalyst composition being represented by the formula of: $x(Mo_{12}Bi_aFe_bCO_cA_dB_eO_f)/yZ$, wherein $Mo_{12}Bi_aFe_bCo_cA_dB_eO_f$ is an oxide compound, wherein Z is a catalyst carrier selected from the group consisting of graphite, boron, silicon, germanium powder, and mixtures thereof, wherein Mo, Bi, Fe, Co, and O are chemical symbols of molybdenum, bismuth, iron, cobalt, and oxygen respectively, wherein A is at least one member selected from the group consisting of W, V, Ti, Zr, Nb, Ni, and Re, wherein B is at least one member selected from the group consisting of K, Rb, Cs, Sr, and Ba, wherein a, b, c, d, and e are the atomic ratios of Mo, Bi, Fe, Co, A, and B respectively, wherein f is determined by the atomic ratios of each component of said oxide compound, wherein x and y represent the quantity of said oxide compound and the quantity of said carrier Z by percentage weight respectively, wherein a, b, c, d, e and f satisfy the requirements of a=0.1 to 15, b=0.05 to 10, c=1 to 15, d=0.01 to 5, e=0.01 to 2; wherein said x and said y has a relationship determined by a formula of y/(x+y).

9. The catalyst composition, as recited in claim 8, wherein said x and said y satisfy the requirements of the formula: y/(x+y)=10% to 70% by weight.

10. The catalyst composition, as recited in claim 9, wherein said oxide compound is prepared by compositions comprising: molybdic compound selected from the group consisting of phospho-molybdic acid, molybdate, and molybdenum oxide; vanadium compound selected from the group consisting of metavanadate and vanadium pentoxide; tungsten compound selected from the group consisting of tungstate and tungsten trioxide; alkaline element selected from the group consisting of hydroxide and nitrate; and other essential elements selected from the group consisting of nitrate, acetate, chloride, and oxide compound.

11. The catalyst composition, as recited in claim 8, wherein said oxide compound is prepared by compositions comprising: molybdic compound selected from the group consisting of phospho-molybdic acid, molybdate, and molybdenum oxide; vanadium compound selected from the group consisting of metavanadate or vanadium pentoxide; tungsten compound selected from the group consisting of tungstate and tungsten trioxide; alkaline element selected from the group consisting of hydroxide and nitrate; and other essential elements selected from the group consisting of nitrate, acetate, chloride, and oxide compound.

12. A process of producing a catalyst composition for manufacturing MAL, comprising the steps of:
(a) individually dissolving each component of an oxide compound in proportional ratio;
(b) mixing said components with each other to form a mixture and adding ammonia water into said mixture to adjust a pH value thereof between 4 and 7;
(c) adding a carrier Z into said mixture in powdered form to form a compound powder, wherein said carrier Z is a catalyst carrier selected from the group consisting of graphite, boron, silicon, germanium powder, and a mixtures thereof; and
(d) drying said compound powder to form said catalyst composition, wherein said catalyst composition is represented by the formula of: $x(Mo_{12}Bi_aFe_bCo_cA_dB_eO_f)/yZ$, wherein $Mo_{12}Bi_aFe_bCo_cA_dB_eO_f$ is said oxide compound, wherein Mo, Bi, Fe, Co, and O are chemical symbols of molybdenum, bismuth, iron, cobalt, and oxygen respectively, wherein A is at least one member selected from the group consisting of W, V, Ti, Zr, Nb, Ni, and Re, wherein B is at least one member selected from the group consisting of K, Rb, Cs, Sr, and Ba, wherein a, b, c, d, and e are the atomic ratios of Mo, Bi, Fe, Co, A, and B respectively, wherein f is determined by the atomic ratios of each component of the oxide compound, wherein x and y represent the quantity of said oxide compound and the quantity of said carrier Z by percentage weight respectively, wherein a, b, c, d, e and f satisfy the requirements of a=0.1 to 15, b=0.05 to 10, c=1 to 15, d=0.01 to 5, e=0.01 to 2, wherein x and y satisfy the requirements of the formula: y/(x+y)=10% to 70% by weight, wherein said catalyst composition is prepared by compositions comprising molybdic compound selected from the group consisting of phosphomolybdic acid, molybdate and molybdenum oxide, vanadium compound selected from the group consisting of metavanadate and vanadium pentoxide, tungsten compound selected from the group consisting of tungstate and tungsten trioxide, alkaline element selected from the group consisting of hydroxide and nitrate, and other essential elements selected from the group consisting of nitrate, acetate, chloride, and oxide compound.

13. The process, as recited in claim 12, wherein the step (d) further comprises the steps of:
   (d.1) first-time calcining said compound powder at 150 to 250 degrees Celsius; and
   (d.2) second-time calcining said compound powder at 400 to 700 degrees Celsius for 1 to 10 hours under air circulation.

14. The process, as recited in claim 13, wherein the step (c) further comprises the steps of:
   (c.1) adding said carrier Z into said mixture and heating said mixture at 50 to 90 degrees Celsius for 1 to 10 hours until said mixture is dried; and
   (c.2) crushing said mixture with said carrier Z to form said compound powder.

15. The process, as recited in claim 13, wherein the step (c) further comprises the steps of:
   (c.1) heating said mixture at 50 to 90 degrees Celsius for 1 to 10 hours until said mixture is dried and treated in powder form by crushing said mixture; and
   (c.2) adding said carrier Z in powder form into said powdered form mixture and evenly mixing said carrier Z with said mixture to form said compound powder.

16. The process, as recited in claim 12, wherein the step (c) further comprises the steps of:
   (c.1) adding said carrier Z into said mixture and heating said mixture at 50 to 90 degrees Celsius for 1 to 10 hours until said mixture is dried; and
   (c.2) crushing said mixture with said carrier Z to form said compound powder.

17. The process, as recited in claim 12, wherein the step (c) further comprises the steps of:
   (c.1) heating said mixture at 50 to 90 degrees Celsius for 1 to 10 hours until said mixture is dried and treated in powder form by crushing said mixture; and
   (c.2) adding said carrier Z in powder form into said powdered form mixture and evenly mixing said carrier Z with said mixture to form said compound powder.

* * * * *